United States Patent
Hillebrand et al.

(10) Patent No.: US 9,260,750 B2
(45) Date of Patent: Feb. 16, 2016

(54) MOBILE RAPID TEST SYSTEM FOR NUCLEIC ACID ANALYSIS

(71) Applicants: Timo Hillebrand, Hoenow (DE); Claus Knippschild, Jena (DE); Benjamin Jaschinsky, Halle (DE); Elmara Graser, Berlin (DE)

(72) Inventors: Timo Hillebrand, Hoenow (DE); Claus Knippschild, Jena (DE); Benjamin Jaschinsky, Halle (DE); Elmara Graser, Berlin (DE)

(73) Assignee: AJ INNUSCREEN, GmbH, Berlin (DE)

(*) Notice: Subject to any disclaimer, the term of this patent is extended or adjusted under 35 U.S.C. 154(b) by 235 days.

(21) Appl. No.: 13/723,315

(22) Filed: Dec. 21, 2012

(65) Prior Publication Data

US 2013/0130257 A1 May 23, 2013

Related U.S. Application Data

(63) Continuation of application No. 12/820,569, filed on Jun. 22, 2010, now abandoned, which is a continuation of application No. PCT/EP2008/068197, filed on Dec. 22, 2008.

(30) Foreign Application Priority Data

Dec. 20, 2007  (DE) .......................... 10 2007 062 441

(51) Int. Cl.
 *C12Q 1/68* (2006.01)
 *B01L 3/00* (2006.01)
 *B01L 7/00* (2006.01)

(52) U.S. Cl.
 CPC ............... *C12Q 1/686* (2013.01); *B01L 3/5023* (2013.01); *B01L 7/52* (2013.01); *B01L 2200/026* (2013.01); *B01L 2200/04* (2013.01); *B01L 2200/10* (2013.01); *B01L 2300/0636* (2013.01); *B01L 2300/0825* (2013.01); *B01L 2300/1822* (2013.01)

(58) Field of Classification Search
 None
 See application file for complete search history.

(56) References Cited

U.S. PATENT DOCUMENTS

| | | | |
|---|---|---|---|
| 4,622,822 A * | 11/1986 | Beitner | ............................. 62/3.2 |
| 5,589,136 A | 12/1996 | Northrup et al. | |
| 6,602,473 B1 | 8/2003 | Northrup | |
| 6,692,700 B2 | 2/2004 | Handique | |
| 2005/0227275 A1 | 10/2005 | Jung et al. | |
| 2006/0252064 A1 | 11/2006 | Wu et al. | |
| 2007/0054296 A1 | 3/2007 | Piepenburg et al. | |
| 2007/0166204 A1 | 7/2007 | Li | |
| 2009/0000764 A1 | 1/2009 | Tochon et al. | |

FOREIGN PATENT DOCUMENTS

| | | | |
|---|---|---|---|
| WO | WO 2004/065010 A2 | 8/2004 | |
| WO | WO 2004/099438 A1 | 11/2004 | |
| WO | WO 2007/078850 A2 | 7/2007 | |
| WO | WO 2007/092713 A2 | 8/2007 | |
| WO | WO 2007/116298 A2 | 10/2007 | |
| WO | WO2008076395 | * 6/2008 | ............. B01D 69/04 |

OTHER PUBLICATIONS

Benett et al. Handheld advanced nucleic acid analyzer. 2000. Proc. SPIE. vol. 4200, pp. 55-63.*
Chen, Zongyuan, et al. A Microfluidic System for Saliva Based Detection of Infectious Diseases. Annals of the New York Academy of Sciences 1098.1 (2007): 429-436.*
Dougherty, George M., David S. Clague, and Robin R. Miles. Field-capable biodetection devices for homeland security missions. Apr. 2007. Defense and Security Symposium. International Society for Optics and Photonics. pp. 654016-654016.*
Khandurina J, McKnight TE, Jacobson SC, Waters LC, Foote RS, Ramsey JM. Integrated system for rapid PCR-based DNA analysis in microfluidic devices. Anal Chem. Jul. 1, 2000; 72(13):2995-3000.*
Northrup MA, Benett B, Hadley D, Landre P, Lehew S, Richards J, Stratton P. A miniature analytical instrument for nucleic acids based on micromachined silicon reaction chambers. Anal Chem. Mar. 1, 1998; 70(5):918-22.*
Raja S, Ching J, Xi L, Hughes SJ, Chang R, Wong W, McMillan W, Gooding WE, McCarty KS Jr, Chestney M, Luketich JD, Godfrey TE. Technology for automated, rapid, and quantitative PCR or reverse transcription-PCR clinical testing. Clin Chem. May 2005; 51(5):882-90. Epub Mar. 3, 2005.*
Wang, J., Chen, Z., Corstjens, P. L., Mauk, M. G., & Bau, H. H. (2006). A disposable microfluidic cassette for DNA amplification and detection. Lab on a Chip, 6(1), 46-53.*

(Continued)

*Primary Examiner* — Samuel Woolwine
*Assistant Examiner* — Olayinka Oyeyemi
(74) *Attorney, Agent, or Firm* — Oblon, McClelland, Maier & Neustadt, L.L.P.

(57) ABSTRACT

A mobile rapid test system for nucleic acid analysis. A method comprising the steps of amplification of the nucleic acids by means of rapid-PCR technology, conversion of a double-stranded amplification product into a single-stranded DNA fragment, hybridization with a labeled probe and detection of the nucleic acids on a lateral-flow test strip. A device comprising a reaction cavity which preferably consists of a thin film, inlet and outlet openings for the reaction cavity, one or more heatable sample blocks which are connected to miniaturized cooling bodies and a window for reading off the result. The lateral-flow test strip is a component of the mobile rapid test system. Operation of the instrument system requires no external power source, but only batteries or a rechargeable battery.

20 Claims, 1 Drawing Sheet

(56) References Cited

OTHER PUBLICATIONS

Weigl, B. H., et al. Fully integrated multiplexed lab-on-a-card assay for enteric pathogens. Jan. 2006. MOEMS-MEMS 2006 Micro and Nanofabrication. International Society for Optics and Photonics, pp. 611202-611202.*

Glynou K., et al., "Oligonucleotide-Functionalized Gold Nonoparticles as Probes in a Dry-Reagent Strip Biosensor for DNA Analysis by Hybridization", Analytical Chemistry, vol. 75, No. 16, Aug. 15, 2003, pp. 4155-4160, XP000175793.

Wittwer C., et al., "Real-time Multiplex PCR Assays", Methods, vol. 25. No. 4, 2001, pp. 430-442, XP002265718.

Wang et al. (Lab Chip. Jan. 2006;6(1):46-53. Epub Dec. 5, 2005); teaches a microfluidic PCR device comprising a lateral-flow test strip.

Chen et al. (Ann N Y Acad Sci. Mar. 2007;1098:429-36); teaches a microfluidic PCR device comprising a lateral-flow test strip.

* cited by examiner

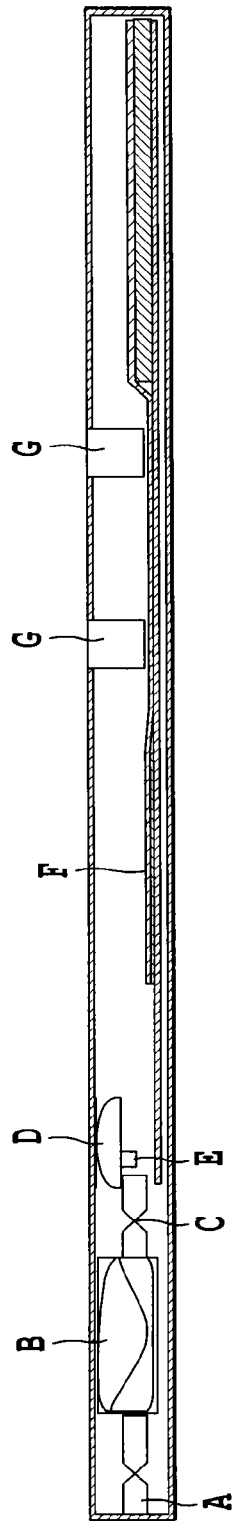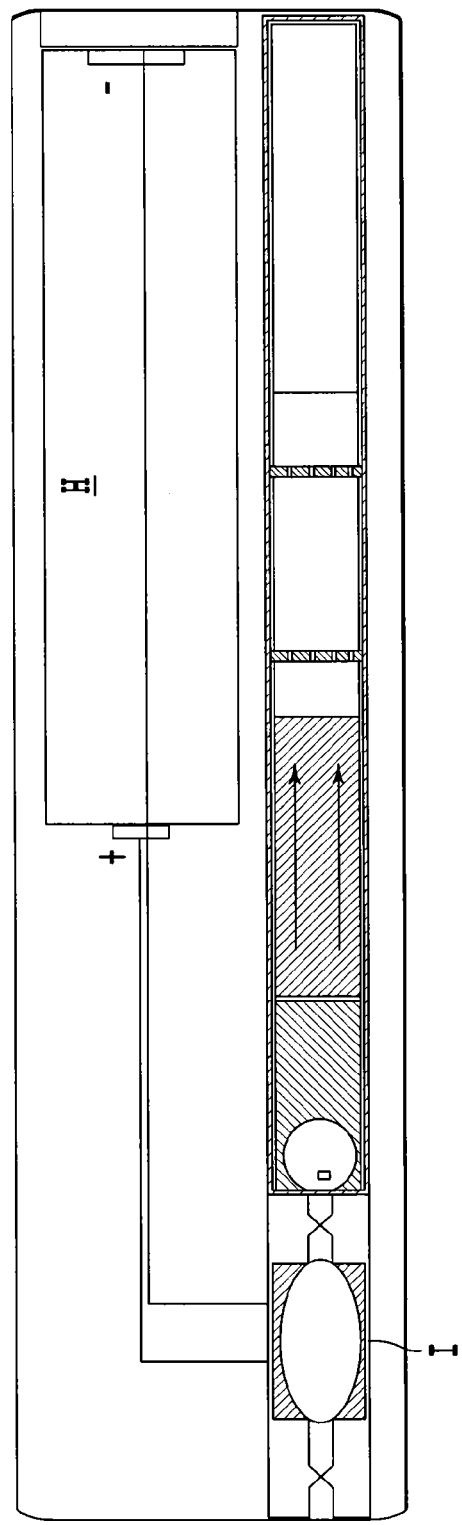

MOBILE RAPID TEST SYSTEM FOR NUCLEIC ACID ANALYSIS

CROSS-REFERENCE TO RELATED APPLICATIONS

This application claims benefit under 35 U.S.C. §365(c) and 35 U.S.C. §120 to PCT/EP2008/068197, filed Dec. 22, 2008, which claims priority to Germany 10 2007 062 441.9, filed Dec. 22, 2007. Both of these documents are hereby incorporated by reference in their entireties.

BACKGROUND OF THE INVENTION

1. Field of the Invention
A mobile equipment system for gene diagnostics.
2. Description of the Related Art
The examination of diagnostically relevant biological samples, such as serum, plasma, blood, swab samples, or organ smears, for the detection of infectious pathogens has gained tremendous importance in recent years. Viral infections such as HIV, HCV, or HBV are increasing worldwide. Furthermore, bacterial infections are also increasing again, among other things also as the result of climatic changes. The occurrence of new, deadly infectious diseases having an extremely high infection potential (SARS, bird flu) shows more and more clearly that rapid diagnostics, which can be carried out on site, are decisive for preventing epidemics. Furthermore, diagnostic systems that are easy to handle and relatively inexpensive also play an important role, particularly for developing countries, in combating the spread of infectious diseases. The majority of the tests currently being used primarily for the detection of viral infectious diseases (HIV, HCV, HBV) are based on carrying out REAL-TIME PCRs. These tests are tied to extremely expensive equipment technology prerequisites, and also expensive reagents. These methods can only be carried out by trained technical personnel in special laboratories. On-site diagnostics are not possible. New generations of integrative system solutions (combinations of nucleic acid isolation, amplification, and chip detection) for mobile on-site diagnostics are in development, but not in a stage of successful marketing. Furthermore, these systems often focus on the sector of military diagnostics, and, in analogy to the "traditional REAL-TIME PCR" methods, are also very expensive, in terms of both devices and reagents.

The so-called rapid PCR technology allows carrying out amplification reactions within only a few minutes and is therefore clearly faster than standard PCR methods. For the miniaturized device solution, the invention is accomplished by means of a novel reaction cavity (consumable). In the sector of PCR consumables, various methods are known for their production. The most widespread is the production method using injection-molding. The consumables produced in this manner are commercially available in a large number of shapes and arrangements. However, these receptacles all have a very thick wall thickness (approximately 0.2 mm-0.35 mm), which opposes good heat transfer from the heated sample block into the sample, as a very great resistance. If these receptacles are used as intended, in a thermocycler, the sample block situated in the devices heats up at a speed of up to 5° C./s. The resulting speed in the sample, however, is significantly reduced by the receptacles, so that the sample (situated in the receptacle) is only heated up at approximately 1.5-2° C./s. Even those receptacles offered for sale as "thin-wall" receptacles (minimal wall thickness of approximately 0.19 mm; Eppendorf product catalog 07-08, p. 200) are not able to significantly improve this condition. The technical prerequisites (heating and cooling) for rapid processing of the temperatures in PCR are implemented technically, but the efficacy is greatly impaired, because of the consumable used.

Usual sample volumes used in PCR lie in the range of 5-50 µl. The receptacles, produced by means of injection-molding, possess their maximal wall thickness at the bottom, so that tempering and implementation of a PCR reaction of low volumes, 1-10 µl (which collect at the bottom of the receptacles), can be carried out only very imprecisely and slowly.

The metallic sample blocks used (aluminum, silver) in thermocyclers having a very great heat capacity furthermore ensure that rapid temperature changes in the sample are impossible to implement, even when using strong heating elements. The rapidity of existing systems on the market, which work on the basis of metallic sample blocks and injection-molded consumables, thus comes up against objective limits. From this, it follows that because of their tremendous thermal inefficiency, miniaturized, mobile variants of these thermocyclers exceed the electrical conductivity of accessible battery technology in unacceptable manner.

Other stationary systems bet on advanced technology to increase the thermal efficiency and make rapid PCR possible.

The most well-known commercially available PCR system that will be mentioned here is the LightCycler from Roche Molecular Biochemicals (cat. No. 1909339 and cat. No. 2011468). This system is based on the use of very thin glass capillaries as PCR consumables and carries out tempering by means of hot air that flows around the capillaries. These capillaries can hold a volume of 10-20 µl and are characterized by their large surface area, which allows good heat transfer. However, this large glass surface area absorbs components of standard PCR batches and thus causes the reaction to become more and more inactive. In order to compensate this effect, different carrier molecules, etc., for example, have to be used (EP 1133359). Another disadvantage in this connection is the handling of the very thin capillaries and their price. Miniaturization and simple handling of the receptacles continues to be impossible, however.

A technology that is not based on standard consumables and can be used for mobile use is explained in the published patent application US2005/0227275 A1. Here, a woven metal textile is introduced into the wall of the PCR reaction chamber, by means of production technology. This ensures direct heat transfer to the sample. Although it is pointed out that the wall should be thin, it is not explained how thin. At the same time, cooling of the sample is not discussed in any way. Thus, while this reference explains that rapid PCR is supposed to be carried out, it does not, however, provide sufficient information about technical implementation. This point also includes the fact that the consumable described there does not meet the requirements of being a cost-advantageous consumable material. Introduction of a defined woven heating material and a device for temperature control stand in the way of this requirement. Furthermore, the object according to the invention of the published patent application U.S. 2005/0227275 A1 is furthermore carrying out a PCR reaction and detecting amplification products by means of a lateral-flow strip. PCR with marked primers and nucleotides is described (claim 1, FIGS. 1, 2, 3, 4, 6). However, a disadvantage of this method is that the PCR product is not hybridized with a marked probe. The sole detection of an amplification product in this manner is diagnostically very uncertain, however, since the required 100% specificity of the amplification product is not guaranteed. For this purpose, a specific hybridization reaction is required. Furthermore, there is the latent risk that false-positive results occur due to mis-priming and primer dimers.

The use of a design similar to a "chip" for accommodating a PCR chamber does not represent level of invention, because it is cited many times in the patent literature. Instead, the configuration of the heating/cooling mechanism, of the entire heat transfer, the feed of liquid/solid biochemical reaction components, and the implementation of the process parameter control represent innovation. Thus, for example, the reference WO 2007/092713 A2 discusses a consumable design in chip form that can comprise not only cell sorting and immunological protein detection but also a PCR chamber. Different cell types (precursors of cancer cells, and cancer cells) are separated by means of a lateral-flow test strip method, using appropriate antibodies, and discriminated. However, the lateral-flow method does not serve to detect amplification events. The detection of RNA expression from RNA, which previously took place in a so-called lab-on-a-chip system, is uncoupled from this lab-on-a-chip and takes place as described, on a "laboratory table, using known methods." It is described that alternatively to this, an amplification reactor and a detector can be integral components of the lab-on-a-chip system. This reference does not discuss the configuration of the PCR chamber in the sense of the aforementioned properties. There is also no mention of a PCR reaction in the claims. Nevertheless, a mobile variant of the equipment system (with consumable) can be discussed here. For operation of the device independent of the power network, power consumption must be optimized and be as low as possible. Because of the use of a large number of thermoelectric modules ("hydrogel ice valves") and fluid pumps, a person skilled in the art recognizes that this device cannot be suitable for mobile battery operation.

The authors of the reference described above discuss the topic of chip production and of the PCR chamber within this or a similar chip in a publication (Chen, Z., et al.; Ann. N.Y. Acad. Sci. (March 2007) 1098; 429-436). A system is presented that comprises a PCR chamber and a lateral-flow test strip. Measured by the requirements—rapid (rapid PCR), mobile (battery operation), cost-advantageous (consumable), and easy to handle—this invention must be assessed as follows. It is known to an expert that rapid PCR is defined by the total time of the reaction (with 30 cycles in less than 30 minutes) and by the temperature changes in the sample that are achieved (>4 K/second). Without any statement of heating or cooling rates, a cycle time of at least one minute (sum of the stop times without duration of the temperature change), as well as the use of a PCR chamber made of polycarbonate, produced by means of milling technology (wall thickness values of at least 100 μm), it becomes clear to a person skilled in the art that this equipment system cannot be used for rapid PCR. In this publication, a mobile system is not described in any manner. Just like in the patent document described above, more than 10 thermoelectric modules, plus two multidirectional setting valves, a fluid pump, a vacuum pump, and a laser scanner are supposed to be accommodated here, on the equipment side. These modules, which are very power-intensive, as well as the consumable design, which is not optimized, thus preclude even the possibility of mobile battery operation. Finally, a person skilled in the art recognizes that this system cannot be used for mobile use, since the complexity of the consumable (multiple production steps, introduction of hydrogels) requires unreasonable production costs. Detection of the amplification takes place by way of the use of two marked primers. However, it is known to a person skilled in the art that such a detection method on a test strip is highly problematical, since specific amplification products cannot be separated from the non-specific amplificates and so-called primer dimers. Thus, such a detection system cannot be used in diagnostics.

Furthermore, the publication by Wang et al. belongs to the state of the art (Wang, J. et al.; Lab on a Chip (2006) 6: 46-53. The system presented there can be identified by a person skilled in the art as a variant of the two developments described above (for example the same use of ice valves or marked primers as a detection system). Here, the precise properties of the PCR reaction unit are stated once more in concrete terms. A thickness of 250 μm is indicated for the wall between the heating/cooling element and the sample. On the technology side, this chamber and all the channels are introduced into a polycarbonate carrier by means of a CNC milling process. Therefore, the thermal resistance of this chamber still lies above that of commercially available reaction receptacles (wall thickness 200 μm to 300 μm; material polyethylene), in which rapid PCR is only possible by means of high-power equipment. Thus, use of the concept for battery operation is excluded once again. The inefficiency of the concept becomes evident to a person skilled in the art when the authors discuss the difficulties in achieving an acceptable cooling rate. Even with active heat transport by means of Peltier elements and the inclusion of a 14 watt fan (conventional fans for processors require 6 watts), only 2.6 K/second is achieved in the sample (see rapid PCR). The concept must also be critically illuminated with regard to the formulated goal of cost minimization. According to the publication, many different production chains have to be run through in order to produce a chip with this concept. Aside from milling of the precision channels, the surfaces additionally have to be polished, hydrogels have to be introduced, two chip halves have to be joined, using a complicated thermal method, and subsequently, reactivation of the gels has to be implemented. This makes it evident to a person skilled in the art that this chip concept makes a cost-advantageous consumable impossible.

BRIEF DESCRIPTION OF THE INVENTION

The invention was based on the task of developing a novel mobile gene-diagnostic rapid test system (combination of hardware and reagents), which is supposed to be easy to operate, allows extremely rapid diagnostic information, and is inexpensive both with regard to the device and with regard to the test to be performed. Therefore, the possibility of being able to carry out diagnostics of infectious diseases in developing countries, without qualitative restrictions, is also supposed to be created.

The mobile rapid test system, according to the invention, for nucleic acid analysis comprises a device for amplification and hybridization of nucleic acids, with amplification primers and at least one hybridization probe, as well as a test kit for detection of the amplification event, and is characterized in that
a) the amplification product and the hybridization probe contain at least one marker, in each instance, and
b) the test kit comprises at least one lateral-flow test strip, which contains a zone for coupling the markers, in each instance.

BRIEF DESCRIPTION OF THE DRAWINGS

The invention will be explained in greater detail using two figures. In the appendix, the fundamental diagrams for the means according to the invention are shown. In this connection, the drawings are not considered a limitation for other embodiments.

FIG. 1 shows the schematic representation of the cartridge.

FIG. 2 shows the schematic representation of the device (voltage source and reaction cartridge).

REFERENCE SYMBOL LIST

A: Inlet opening
B: Consumable for the amplification/hybridization reaction
C: Outlet opening and connection between consumable and test strip
D: Reservoir for running buffer
E: Outlet opening from reservoir for running buffer, with feed to the test strip
F: Test strip
G: Viewing window for detection of the detection signal on the test strip
H: Battery as a voltage source
I: Heating/cooling element

DETAILED DESCRIPTION OF THE INVENTION

The term "marker" is understood to mean any atom or molecule that can be used to generate a detectable (preferably quantifiable) signal on a lateral-flow test strip, and that can be bound to a nucleic acid.

Markers can preferably generate signals by means of fluorescence, colorimetry, or enzymatic activity. Markers by means of biotin and FITC (fluorescein isothiocyanate) are preferred.

Marking of the amplification product takes place either by means of marking of a primer or from marking of the nucleic acid to be determined.

The devices and the test kit are integral components of the mobile rapid test system, and this system represents a miniaturized, mobile-operated, hand-held device that requires no external voltage source during operation, but rather is operated by means of a battery or a rechargeable battery.

Mobile rapid test system contains a reaction cavity for carrying out amplification of nucleic acids, preferably by means of rapid PCR technology, one or more inlet and/or outlet openings for the reaction cavity, one or more heatable sample blocks that are connected with miniaturized cooling bodies, and a possibility for reading off the result, whereby the reaction cavity contains a plastic film having a film thickness that is less than 300 µm, preferably less than 250 µm, 200 µm, 150 µm or 100 µm. These film thickness values include all intermediate values and subranges. The plastic film preferably consists of polypropylene, and is welded, with a stable shape, in a desired geometry, and pressed onto the sample block with light contact pressure, from above.

An amplification primer is preferably marked by means of biotin, and the hybridization probe is preferably marked with FITC, and is protected ("blocked") against polymerization at the 3' end. This "blocking" can be achieved, for example, by using non-complementary bases or by adding a chemical group, such as a phosphate group, at the 3'-hydroxyl of the last nucleotide. Blocking can also be achieved by removing the 3'-OH or by using a nucleotide without the 3'-OH, such as a dideoxy nucleotide.

The lateral-flow test strip carries separate binding locations, preferably two, a streptavidin location for coupling the marked amplification products, and a binding location for function monitoring of the test strip, as well as a zone with conjugated detection particles (for example anti-FITC gold particles).

The object of the invention is also a method for detection of nucleic acids by means of the mobile rapid test system described above, having the following steps:

Amplification of the nucleic acids by means of the rapid PCR technology, with amplification primers, of which either at least one is marked or the nucleic acids were marked, Conversion of a double-strand amplification product into a single-strand DNA fragment (denaturing), Hybridization of the denatured amplification product with at least one marked hybridization probe, Detection of the nucleic acids on a lateral-flow test strip, which contains a zone for coupling of the markers, in each instance.

The invention solves the problems described in ideal manner, by means of the simple and synergistic combination of an equipment system for carrying out specific amplification reactions and simple detection chemistry for detection of a specific amplification event, whereby the equipment system is present in the form of a so-called hand-held system, and this is not only miniaturized but also can be operated in mobile manner, i.e. without the need for an external voltage source, particularly by means of battery operation.

In this connection, the invention is based on the use of the so-called rapid PCR technology.

The invention solves the existing problems of a miniaturized, hand-held rapid PCR thermocycler in combination with a detection model as follows:

The invention is based on a novel arrangement and concept of heating elements and sample block, which are suitable for mobile use in terms of power and size, in combination with a completely novel consumable (reaction cavity for the amplification reaction) having a significantly improved heat transfer. This is achieved, according to the invention, in that the novel consumable is optimized in such a manner that the biggest problem, the physical resistance for effective PCR tempering, can be overcome. An optimal heat transfer is present when a sample can be applied directly to the sample block or tempered medium, without interfering materials and additional heat transfers. Such implementation has been impossible up to now for reasons of contamination.

Only minimal interference of the heat transfer would exist if an extremely thin layer of a biocompatible material could be used. This is solved, according to the invention, in that an extremely thin-layered PP film is used. In this connection, this film is laid or folded into a desired geometry, and welded in stable shape. This specific geometry is characterized in that it possesses the largest possible flat surface area at the bottom, for the sample volume of the amplification batch to be filled in. This large surface area serves as a heat transfer surface to the heated sample block. Because of the ultra-thin film, minimal resistance to the heat transfer takes place. All non-heated surfaces of the reaction chamber are reduced to a minimum, so that no unnecessary heat flow to the surroundings can take place. Thus, it is possible to implement a heating rate effectiveness from the sample block to the sample of almost 100%, within the sample.

Preferably, the non-heated surface areas are <1.4, 1.4. 1.5, 1.6, 1.7, 1.8, 1.9, 2.0 or >2.0 times larger, particularly 1.7 times larger, than the heated surface areas.

A Peltier element operated by a battery is used as sample block to be used; it is screwed onto a cooling body adapted to the system as a whole. The geometry of the sample block that is used is also characterized by a maximal surface area, as a counterpart of the consumable. The volume and thus also the capacity of the sample block are reduced to an absolute minimum, according to the invention. Therefore the sample block can theoretically be heated at a heating rate of 15° C./s. The geometry of the consumable has been selected to be so large, according to the invention, that strong contact pressure onto the sample block is implemented by means of slight downward pressure from above and physical effects that are utilized and therefore uniform heating at these speeds is also promoted and implemented in this way.

Thus the prerequisites for implementing an amplification reaction with a small, mobile device, using a normal battery, and carrying out an ultra-rapid reaction, have been created. However, it is clear to a person skilled in the art that mobile on-site diagnostics cannot be carried out solely with a miniaturized and mobile possibility of implementing the PCR reaction. For this purpose, the system also requires detection of a specific target amplification that has taken place.

In this connection, the detection must be an integral component of the system as a whole. This combination of amplification and detection is surprisingly implemented in very simple manner, according to the invention, by means of the use of so-called lateral-flow strips that are known to a person skilled in the art. Although the two technologies (rapid PCR and lateral-flow strips) exist as standard techniques, there is no link between the two technologies in the form of an integrative overall system that fulfills the requirements for a specific diagnostic system. As has already been explained, a number of similar equipment systems use detection strategies that do not allow correct diagnostics or do not use an amplification reaction of nucleic acids (U.S. 2005/0227275 A1, WO 2007/092713 A2, Chen, Z., et al.; Ann. N.Y. Acad. Sci. (March 2007) 1098: 429-436, Wang, J. et al.; Lab on a Chip (2006) 6: 46-53).

However, precise diagnostics are made possible by the invention. Therefore the invention not only combines an amplification module with a lateral-flow strip, but also is based on a detection strategy that takes the diagnostic requirements into account. To underline the differences, it will be emphasized once again, in the following, how lateral-flow strips are used for DNA/RNA diagnostics.

Carrying out gene tests by means of so-called lateral-flow strips has been propagated in different forms up to now. One possibility (published patent application KR 1020060099022 A; Method for the detection and analysis of nucleotide sequence using membrane lateral flow, and kit for same) used lateral-flow methods for detecting nucleic acids. This method uses the technology of hybridization of nucleic acids on a solid phase. In this connection, specific captor nucleic acids are immobilized on the test strip and hybridized with single-strand target nucleic acids. A captor nucleic acid is a single-strand ribonucleic acid or deoxyribonucleic acid, or one that only becomes single-strand during the course of the process, which possibly contains chemically modified bases or base analogs, chemically modified sugars or sugar analogs, or is modified in some other way, and is characterized in that it binds to a specific, predetermined nucleic acid or class of nucleic acids at high specificity and selectivity. In this connection, this process requires the conversion of a double-strand DNA fragment (as the result of a specific amplification reaction) into a single-strand DNA fragment. For this purpose, the process must be carried out subsequent to a PCR reaction. Another rapid detection method that also uses the detection of amplification products by means of a test strip and is available commercially is based on a completely different principle, in contrast to the above patent document. Here, implementation of the PCR reaction is carried out with a biotinylated primer and a non-biotinylated primer. After the PCR is carried out, a PCR product is present, which is biotin-marked at one end. The detection uses a test strip (for example from Millenia), which contains two separate binding locations. A streptavidin location for coupling the biotin-marked DNA strand and an FITC binding location for monitoring the function of the test strip.

The detection of the PCR product is implemented in that after PCR has been carried out, the PCR batch is denatured and hybridized with a probe that is complementary to the biotin-marked DNA strand. The probe is FITC-marked.

For detection, the PCR batch is mixed with a running buffer and applied to the test strip. According to the test description, the biotinylated DNA strand binds to the streptavidin binding location of the strip. Detection takes place by way of the FITC marker of the probe hybridized with the DNA strand. A typical signal is formed, in the shape of a strip. This signal is supposed to be the specific detection of the amplification product. However, the method does not combine hybridization of the probe with the process of PCR, but rather carries this out as a separate method step. However, the method has a fundamental and dramatic error source.

The detection of the target nucleic acid to be detected is not specific. The cause for this lies in the fact that artifacts that were formed during PCR, for example primer dimers, of course also bind specifically to the streptavidin binding location of the test strip, and therefore can cause a positive reaction, just like a specific PCR product (as already described multiple times in the above text).

From these explanations, it follows that while there are applicative solutions for carrying out gene tests on strips, these require not only amplification but also denaturing of the amplification product, and thus do not permit a direct combination of amplification and detection. Furthermore, as shown in Example 2, certain methods are not specific, and are very problematical with regard to the production of false-positive diagnostic results.

A novel and very elegant possibility is based on a probe hybridization between amplificate and specific hybridization probe that is integrated into the amplification reaction. The detection of the specific hybridization event then takes place on a test strip.

In this way, the possibility is created, for the first time, of working without further manipulation (denaturing of double-strand DNA) and circumventing the amplification problems that have already been presented, and thus of being able to combine the amplification/hybridization reaction directly with detection on a test strip. Detection of an amplification/hybridization product takes place in that an amplification primer and the specific hybridization probe at the 3'-end are provided with a marking molecule, in each instance (for example biotin and FITC). The amplification reaction takes place under standard conditions. In this connection, the actual amplification reaction is followed by a denaturing step for thermal strand separation of the amplification product generated during PCR. After denaturing, the PCR reaction batch is cooled to the hybridization temperature of the probe. During this step, the hybridization probe binds specifically to the complementary DNA strand of the amplification product. In this connection, this strand carries the biotin marker that was installed in the PCR product by means of the biotin-marked primer. After the amplification/hybridization reaction has been carried out, the reaction batch is transferred to the test strip. On this test strip, detection of the specific hybridization event can take place as follows: The test strip carries two separate binding locations, for example, in one embodiment variant; a streptavidin location for coupling the biotin-marked amplification products, and an FITC binding location for monitoring the function of the test strip. Furthermore, the test strip contains a zone with conjugated detection particles (for example anti-FITC gold particles). After the PCR batch is brought into contact with such a test strip, the following binding events can occur:

1. All the FITC-marked nucleic acids (non-hybridized FITC-marked hybridization probe and/or hybridization product between biotin-marked DNA strand and FITC-marked hybridization probe) bond to gold particles that are coated with anti-FITC antibodies, in the lower sample application region of the test strip.
2. In the further progression of the test strip, there is the streptavidin binding location. The following nucleic acids can bind to this binding location:
   (a) the biotin-marked primers,
   (b) the biotin-marked DNA strands, and
   (c) the hybridization products between biotin-marked DNA strand and FITC-marked hybridization probe.

However, a detection signal can only become visible if the specific hybridization product between biotin-marked DNA strand and FITC-marked hybridization probe is present, since only this product is also coupled with the detection system (FITC/anti-FITC gold particles).

3. In the further progression of the test strips, excess gold particles coated with anti-FITC antibodies then also bind; these serve as a control to check the ability of the test strip to function.

This embodiment variant, as has already been mentioned, is very elegant and does not entail the potential risk of false-positive signals. It is therefore the variant to be preferred for use of a lateral-flow test strip, for the mobile detection system according to the invention.

The invention should be understood as a combination of the novel method for detection of amplificates and a novel device for mobile use. In the implementation of the device according to the invention, the detection strategy by means of lateral-flow strips, intelligent sample application, and energy-efficient tempering of sample volumes are combined, to produce a consumable that is cost-advantageous because it is simple to produce.

An embodiment of the device according to the invention looks as follows:

The consumable represents a design integration of the functional modules for application of the reaction mixture initially produced (nucleic acid to be investigated, dNTPs, primer, hybridization probe, as well as amplification buffer), for implementation of an energy-efficient amplification reaction, for storage and application of a running buffer, as well as for the detection reaction by means of test strips. The battery-operated device is configured in such a manner that it represents an ideal means for processing the functional sections of the consumable. The sequence of processing begins with application of the reaction mixture by way of the inlet opening, whereby the mixture is guided into the amplification chamber directly or by way of additional process segments. After the amplification/hybridization reaction has taken place, the reaction batch is transferred to the test strip by way of the outlet opening. Subsequently, the running buffer is also passed to the test strip, from a separate reservoir, whereby in one embodiment variant, the running buffer can first pass through the reaction chamber. The reservoir for the running buffer is also situated in the cartridge. After the test strip reaction has been completed, the diagnostic result is read off in a viewing zone. The reaction cartridge, which contains the amplification module and the test strip, as well as the reservoir for the running buffer, is preferably a disposable article, in other words, a new one is inserted into the base device for every reaction and disposed of after the test has been run.

The device according to the invention is an object of the invention described, even without the detection system according to the invention, and can also be combined with the detection system for captor nucleic acids that was mentioned above. In this way, a system is made available that consists of the device according to the invention, according to the embodiments described herein, and a test strip on which special captor nucleic acids are immobilized, and with which detection of the nucleic acids to be determined takes place by means of hybridization with the captor nucleic acids on the test strip. Preferably, such a system will comprise a device that is a miniaturized hand-held device that can be operated in mobile manner, which does not require any external voltage source during operation, but rather is operated by means of a battery or a rechargeable battery, and which integrates said device and said test kit. The hand-held device can comprise a reaction cavity for carrying out an amplification of nucleic acids by means of the rapid PCR technology, one or more inlet and/or outlet openings for the reaction cavity, one or more heatable sample blocks that are connected with miniaturized cooling bodies, and a means for reading the result, wherein the reaction cavity contains a plastic film having a film thickness that is less than 300 µm, preferably a film thickness of less than 100 µm. The plastic film may consist of polypropylene and is welded in a desired geometry, in shape-stable manner, and is pressed against the sample block by means of slight contact pressure from above. The reaction cavity and the test strip can be disposed in a reaction cartridge, and the plastic film produces connection channels with the reaction cartridge. The system may further comprise a reservoir and an outlet opening for running buffer or contain connection channels between a reaction cavity, test strip, and running buffer reservoir, which can be closed off. The reaction cavity may have two surfaces that can be connected with one another at channel or chamber edges, with force fit and/or shape fit, whereby at least one of these surfaces consists of a plastically or elastically deformable material. The reaction cavity can also comprise a depression and the sample block can be configured in convex manner with the chamber opening being circular. This system may contain reaction cavity that contains movable pistons and related hollow cylinders for storage of reactants. It may also comprise a heatable sample block, which is connected with a miniaturized cooling body, that contains a battery-operated Peltier element having a heating rate of <5° C./s, 5° C./s, 10° C./s, 12.5° C./s and up to 15° C./s.

In the following, these embodiment variants according to the invention will be explained, without restricting the invention to these variants.

EXEMPLARY EMBODIMENTS

Example 1

The reaction mixture is fed into the inlet opening. The inlet opening is welded shut by means of a heated wire that is integrated into the device. In this connection, the heated wire is moved to the inlet opening by means of a simple pressure mechanism. In this embodiment, both the consumable used for the amplification/hybridization reaction, according to the invention (reaction cavity), and the test strip are placed in a reaction cartridge, one behind the other.

Example 2

The embodiment variant of the consumable is structured in such a manner that one or all the fluids on the consumable are transported from one functional module to the next by way of novel fluid structures. These structures are produced by means of production technology, in that two surfaces are applied to one another, whereby at least one of these surfaces consists of a plastic or elastically deformable material. At the delimitations of the structures, for example the edges of the channels or chambers, the two surfaces are connected with one another, by means of force fit and/or shape fit. When fluid pressure is applied to the small gap that this structure can represent, then at least one of the surfaces domes up and releases a larger gap for passage between the two surfaces. By means of this novel concept, cost-advantageous production of fluidic elements on the consumable is made possible.

Example 3

In another embodiment variant, the reaction chamber represents a perforation or depression in the carrier material of the consumable. Closure of the chamber is achieved in that the film that lies on top of it is pressed against the edges of the perforation or depression. In an embodiment of this variant, the pressure is produced by the sample block, so that the latter brings about not only the heat transfer but also the chamber closure. The increased demands on the pressure seal during PCR are achieved in that the sample block is configured in convex manner and the chamber opening is circular.

Example 4

Storage and application of the running buffer can be configured as follows, in one embodiment variant: A cavity is created between the film and the carrier material, by means of production methods that create a space. This cavity is filled with running buffer during production/outfitting of the consumable. The outlet opening of the reservoir is closed off with a pressure-dependent valve, which can be implemented, for example, by means of a welding seam that can be re-opened. In order to feed the buffer into the reaction chamber, the buffer chamber has pressure applied to it, by the device or by the user, in such a manner that the valve opens and the buffer is moved to the test strip.

Example 5

In this embodiment variant, movable pistons and related hollow cylinders are part of the consumable. In this connection, these cylinders can be filled with fluid on the production side (for example running buffer, reactants). The inlet opening of the consumable is shaped in such a manner that a sample application tool can be connected in shape-fit manner. This tool is also composed of a hollow cylinder that has a piston. For sampling, the piston is pulled up into the cylinder and then connected with the consumable. The pistons of the consumable and of the sampling tool can be moved by the user or by the device. The sample is pressed into the reaction chamber by means of the piston movement at the sample application tool. Air that has to be displaced from the chamber or from the fluidic regions in this manner escapes into the air-free spaces and/or out of the outlet openings that are fluidically situated behind the detection region. Then, one or more sample blocks are pressed down from one or more sides of the reaction chamber. With this process, the reaction chamber is sealed in airtight manner, as in Example 4, so that energetically advantageous tempering of the sample can take place. When the sample blocks are removed, the sample can now be pressed further in the direction of the detection chamber. For this purpose, the piston of the sample application tool and/or the piston of the cylinder with the running buffer can be moved. Air and/or fluids from the cylinders described displaces the sample from the reaction chamber and moves it toward the test strip. Additional running buffer from the corresponding cylinder is applied to the test strip by means of the movement of the pistons. The user can read off the result of the detection by way of a viewing window in the detection region. In another embodiment variant, the detection region, just like the application tool, can be reversibly removed from and connected with the consumable as a whole, and can be replaced by an alternative detection system.

With the combination of rapid PCR and detection of the amplification event according to the invention, by means of a mobile and battery-operated hand-held system, the prerequisites for very simple and inexpensive gene-diagnostic on-site analysis have been created for the first time. In this connection, of course, the hand-held device is much less expensive than the previously proposed high-technology equipment systems, particularly for military applications. This is also supposed to universally allow use of gene-diagnostic rapid tests in developing countries. By means of the method according to the invention, it is made possible to carry out an extremely rapid amplification reaction. The subsequent detection on a test strip is also very fast and robust. Thus, the invention represents a real rapid test system.

Various modifications and variations of the described systems, devices, primers, probes, markers, other system elements, and methods of their configuration and use as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the medical, biological, chemical or pharmacological arts or related fields are intended to be within the scope of the following claims.

Each document, patent, patent application or patent publication cited by or referred to in this disclosure is incorporated by reference in its entirety, especially with respect to the specific subject matter surrounding the cited reference. However, no admission is made that any such reference constitutes background art and the right to challenge the accuracy and pertinency of the cited documents is reserved.

The invention claimed is:

1. A mobile rapid test system for analysis of a nucleic acid to be determined, comprising:
    a device for amplification and hybridization of nucleic acids,
    amplification primers optionally comprising at least one marker,
    at least one hybridization probe comprising at least one marker,
    and a test kit for detection of an amplification event that comprises at least one lateral-flow test strip having a zone for coupling markers;
    wherein the mobile rapid test system is a hand-held device that can be operated in mobile manner, which does not require any external voltage source during operation, but rather is operated by a battery or a rechargeable battery, and which integrates said device and said test kit;
    and wherein the hand-held device comprises a reaction cavity for carrying out an amplification of nucleic acids by PCR, one or more inlet and/or outlet openings for the reaction cavity, one or more heatable sample blocks that are connected with miniaturized cooling bodies, and a means for reading the result, wherein the reaction cavity contains a plastic film having a film thickness that is less than 300 μm, and wherein the plastic film consists of polypropylene and is welded in a desired geometry, in shape-stable manner, and is pressed against each of the one or more sample blocks by slight contact pressure from above.

2. The mobile rapid test system according to claim 1, further comprising a nucleic acid to be determined.

3. The mobile rapid test system according to claim 1, further comprising a nucleic acid to be determined that is marked.

4. The mobile rapid test system according to claim 1, wherein the amplification primers comprise a marker.

5. The mobile rapid test system according to claim 1, further comprising a marked nucleic acid produced from the nucleic acid to be determined.

6. The mobile rapid test system according to claim 1, wherein said plastic film as a film thickness of less than 100 μm.

7. The mobile rapid test system according to claim 1, wherein the reaction cavity and the test strip are disposed in a reaction cartridge and the plastic film produces connection channels with the reaction cartridge.

8. The mobile rapid test system according to claim 1, further comprising a reservoir and an outlet opening for running buffer.

9. The mobile rapid test system according to claim 8, which contains connection channels between the reaction cavity, the test strip, and the running buffer reservoir which can be closed off.

10. The mobile rapid test system according to claim 1, wherein the reaction cavity contains two surfaces that can be connected with one another at channel or chamber edges, with force fit and/or shape fit, whereby at least one of these surfaces consists of a plastically or elastically deformable material.

11. The mobile rapid test system according to claim 1, wherein the reaction cavity contains a depression and the one or more sample blocks are configured in convex manner and the opening of the reaction cavity is circular.

12. The mobile rapid test system according to claim 1, wherein the reaction cavity contains movable pistons and related hollow cylinders for storage of reactants.

13. The mobile rapid test system according to claim 1, wherein the one or more heatable sample blocks are each connected with a miniaturized cooling body that contains a battery-operated Peltier element having a heating rate of up to 15° C./s.

14. The mobile rapid test system according to claim 1, wherein an amplification primer and a hybridization probe are marked at the 5'-end.

15. The mobile rapid test system according to claim 14, wherein the amplification primer is marked by biotin and the hybridization probe is marked by FITC, and protected against polymerization at the 3'-end.

16. The mobile rapid test system according to claim 1, wherein the lateral-flow test strip carries two separate binding locations, a streptavidin location for coupling of the marked amplification products, and a binding location for monitoring the function of the test strip, as well as a zone with conjugated detection particles.

17. The mobile rapid test system according to claim 16, wherein the conjugated detection particles are anti-FITC gold particles.

18. A method for detection of nucleic acids comprising:
amplifying of the nucleic acids with the system according to claim 1 wherein at least one of the amplification primers contains a marker or wherein the amplified nucleic acids contain a marker, denaturing the amplification products,
hybridizing of the denatured amplification product with at least one marked hybridization probe, detecting of the amplification products on the lateral-flow test strip.

19. The method according to claim 18, wherein the PCR reaction is carried out with a marked primer and an unmarked primer for each DNA fragment to be detected, in each instance, and the test strip contains a binding location for the marker of the primer, in each instance, whereby the detection of the nucleic acids takes place in that the denatured amplification product is hybridized with a marked probe that is complementary to the DNA strand marked with the primers, the PCR batch is mixed with a running buffer and applied to the test strip.

20. The method according to claim 18, wherein the marked amplification primers contain a biotin marker that produces a biotin marked amplification product and wherein after denaturing and cooling of the PCR reaction batch, the hybridization probe specifically binds to the complementary DNA strand of the amplification product that is biotin marked.

* * * * *